United States Patent [19]

Copeland et al.

[11] Patent Number: 5,260,872
[45] Date of Patent: Nov. 9, 1993

[54] AUTOMATED TESTING SYSTEM

[75] Inventors: Anne B. Copeland, Palatine; Danny R. Jackson, Third Lake; Lucinda S. Oheim, Gurnee; Margaret E. Stried, Richmond, all of Ill.; Dennis D. Wagley, Gainsville, Fla.

[73] Assignee: Abbott Laboratories, Abbott Park, Ill.

[21] Appl. No.: 771,962

[22] Filed: Oct. 4, 1991

[51] Int. Cl.⁵ .................. G06F 15/00; G01N 21/00
[52] U.S. Cl. .................. 364/413.07; 435/13; 435/290; 422/65; 436/69
[58] Field of Search .................. 364/413.07; 435/13, 435/290, 291; 422/65, 66, 67, 100, 73; 436/69

[56] References Cited

U.S. PATENT DOCUMENTS

| | | | |
|---|---|---|---|
| 3,605,010 | 9/1971 | Folus | 436/69 |
| 4,101,284 | 7/1978 | Difiglio et al. | 422/100 |
| 4,276,383 | 6/1981 | Leighton et al. | 435/291 |
| 4,680,464 | 7/1987 | Bross | 53/57 |
| 4,689,202 | 8/1987 | Khoja et al. | 422/65 |
| 4,774,055 | 9/1988 | Wakatake et al. | 422/100 |
| 4,837,159 | 6/1989 | Yamada | 422/67 |
| 4,937,048 | 6/1990 | Sakai et al. | 422/65 |
| 4,950,608 | 8/1990 | Kishimoto | 435/290 |
| 5,104,621 | 4/1992 | Pfost et al. | 436/47 |

Primary Examiner—Roy N. Envall, Jr.
Assistant Examiner—Frantzy Poinvil
Attorney, Agent, or Firm—Andreas M. Danckers

[57] ABSTRACT

An automated testing system for the quality testing of production samples of a blood-clot dissolving product having
(a) a frame structure having a horizontally disposed support surface;
(b) a loading station for the placement of test tubes into a test tube rack;
(c) a cooled pipetting station for automated dispensing and mixing of reagents and production samples;
(d) a heated bead-drop station for simultaneous addition of a timing bead to each test tube, having a timer for measuring the time to completion of blood-clot dissolution by detecting the movement of each bead to the bottom of each test tube;
(e) a robotic apparatus having an arm and pick-up and release device at the end thereof which is movable both vertically and horizontally and is adapted to move said test tube rack and tubes between said stations; and
a programmable computer for controlling said dispensing, mixing and moving operations and recording the results of the product being tested.

12 Claims, 5 Drawing Sheets

AUTOMATED TESTING SYSTEM

BACKGROUND OF THE INVENTION

The enzyme urokinase is extremely effective in dissolving fibrin-clots in patients's blood vessels whereby to prevent the often devastating and life-threatening consequences thereof. Urokinase, however, is manufactured in varying potencies or concentrations for different situations and different patients. As it is extremely critical that the manufactured products meet certain specifications and inasmuch as such products are, by necessity, manufactured in relatively small batches, a substantial amount of quality-control testing is required.

It has been determined that the very best method of quality-control testing these manufactured enzyme products is to test the effectiveness of production samples of same in dissolving laboratory-formed fibrin-clots. However, in view of the many steps involved in such testing procedures or assays, they would be very time-consuming if done manually.

SUMMARY OF THE INVENTION

The present invention is directed to a new and novel automated testing system for quality-control testing of a manufactured fibrin-clot dissolving enzyme, urokinase.

This new and novel system is mounted on a unitary frame structure which may be provided with rollers which are movable between lowered/operable and raised/inoperable positions and which is characterized by a horizontally disposed support surface. One or more test-tube rack loading stations are provided on the frame structure. The system also includes a pipetting station which is characterized by an automatic computer-controlled pipetting apparatus and by reservoirs of buffer, plasma, thrombin, fibrinogen, media and plasminogen solutions as well as production samples and standards of the fibrin-clot dissolving product to be tested. The pipetting apparatus is adapted to provide vortex dispensing and mixing of the solutions and the production samples in test tubes carried in the test tube racks in accordance with a computer-controlled test program whereby a fibrin-clot is formed in each test tube. Cooling means at the pipetting station maintains the solutions and the production samples, both in the reservoirs and after having been mixed in varying concentration strengths in the test tubes, at a temperature of 2°-8° C. so that the fibrin-clot dissolving enzyme samples are not activated at the pipetting station. The system is further provided with one or more bead-drop stations characterized by a water bath for each test tube rack heated to a temperature of 37° C. (+/−1°) and having a bead-drop apparatus for introducing into each test tube similar beads of glass with timer means being provided for each test tube. In applicants' preferred embodiment, as disclosed herein, each timer means comprises a fiberoptic timer which is activated upon the introduction of a bead to its test tube with the timer being shut down by the bead falling through its dissolved fibrin-clot and blocking the light from the fiber-optic timer whereby to measure, report and record the length of time required for the fibrin-clot in that test tube to dissolve. The testing system is further provided with one or more robotic pick-and-place apparatus having pick-up and release means at the end of a vertically and horizontally movable arm thereof for moving each test tube rack from a loading station to the pipetting station, then to a bead-drop station, and then back to the loading station. Finally, the testing system is provided with a programmable computer for controlling (1) the robotic apparatus, (2) the pipetting apparatus, (3) the operations at each bead-drop station and (4) for receiving and recording the results of the product testing.

The present invention is directed to a new and novel automated apparatus for quality-control testing of a fibrin-clot dissolving product.

An object of the present invention is to provide a new and novel automated testing system for a fibrin-clot dissolving product, which system is characterized by a cooled fibrin-clot forming station wherein fibrin-clot forming solutions are diluted and mixed in a plurality of test tubes together with varying concentrations of production samples and standards of the fibrin-clot dissolving product, and by a bead-drop station having a heated water bath for the test tubes to speed-up activation of the clot-dissolving enzymes, means for introducing a bead into each test tube, and means for timing the passage of each bead through its fibrin-clot upon dissolving of same.

Another object of the present invention is to provide such a system having robotic pick-and-place means for moving the test tubes, mounted in a rack, to the fibrin-clot forming station and then to the bead-drop station, and a programmable computer for (1) controlling the robotic means, (2) controlling operations at both the fibrin-clot forming and bead-drop stations, and (3) for receiving and recording the results of the product testing.

BRIEF DESCRIPTION OF THE DRAWINGS

The features which are believed to characterize this invention are set forth in the appended claims. The invention itself, together with its features, objects, and attendant advantages, will be best understood by reference to the following detailed description of a presently preferred embodiment thereof, taken in conjunction with the accompanying drawings, in which:

DESCRIPTION OF THE PREFERRED EMBODIMENT

Figure 1:
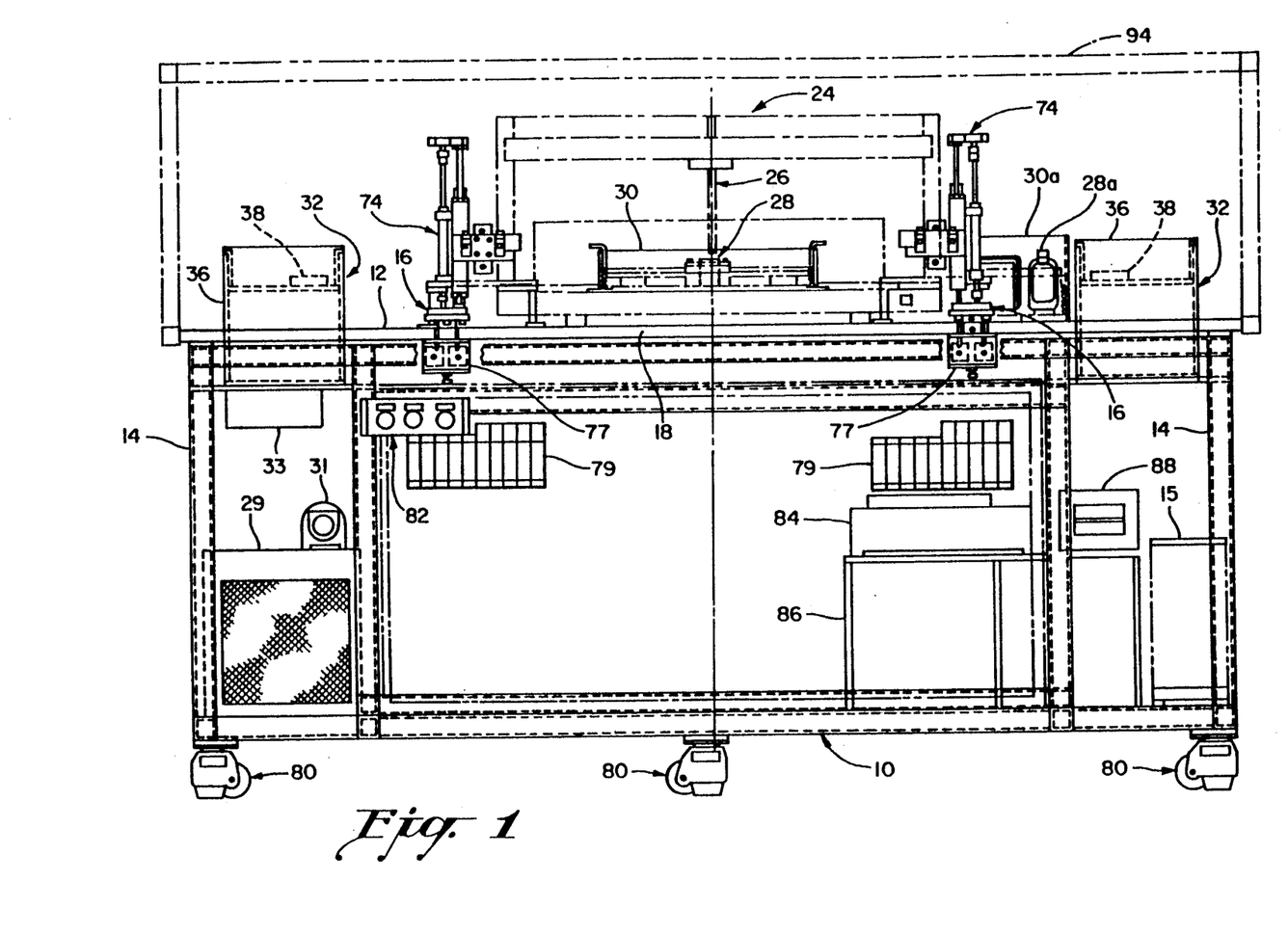
FIG. 1 is a diagrammatic front elevational view of a preferred form of the invention showing several of the components thereof.
Figure 2:
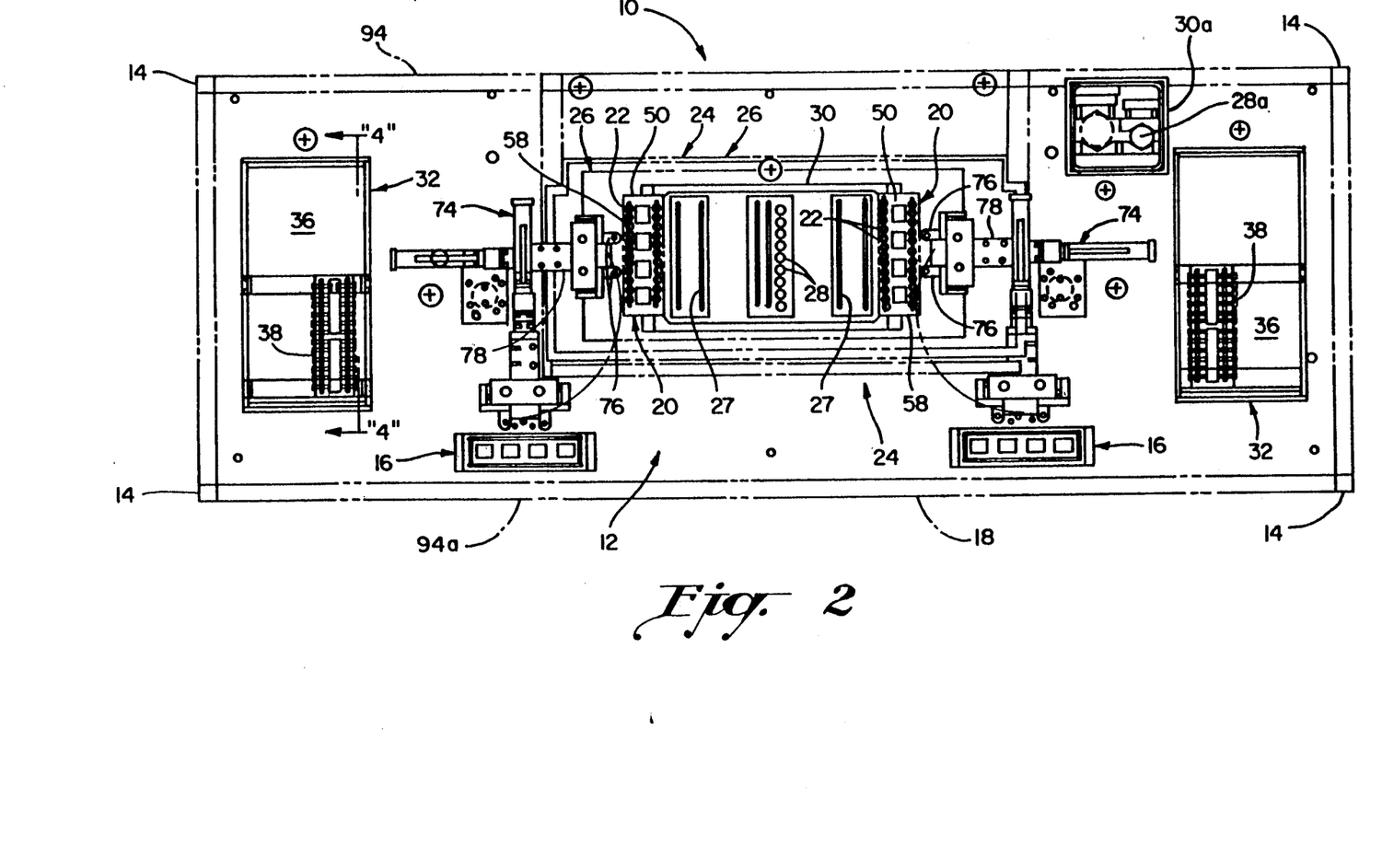
FIG. 2 is a diagrammatic top plan view thereof.
Figure 3:
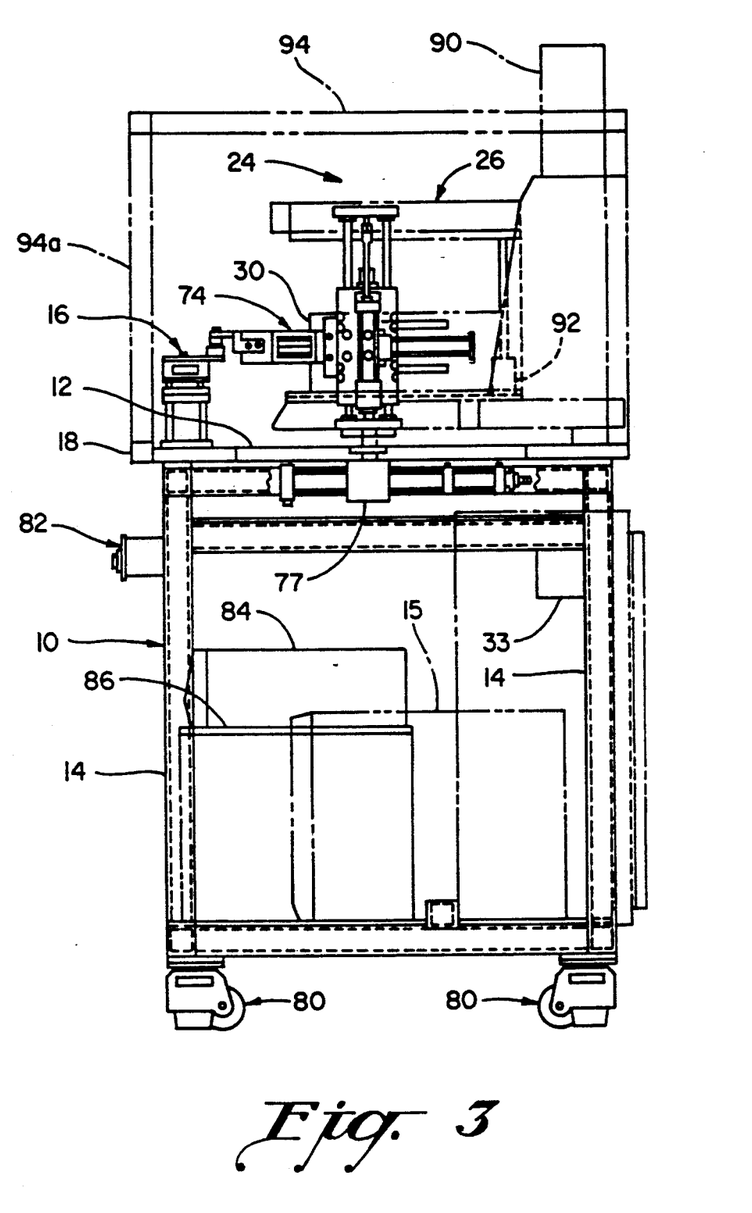
FIG. 3 is a diagrammatic right-end elevational view thereof.

Referring now to the drawings, a preferred embodiment of the invention is best illustrated diagrammatically in FIGS. 1, 2 and 3. As illustrated, this embodiment is characterized by a table-like, unitary frame structure 10 having a horizontally disposed support surface 12 and vertically disposed leg members 14 at the corners thereof. Supported on the frame structure 10 are most of the sub-assemblies or components of the automated system for quality-control testing of a manufactured blood or fibrin-clot dissolving enzyme, specifically urokinase, including a back-up power supply 15, such as a UPS 600 System. The embodiment shown in FIGS. 1, 2 and 3 is a dual system whereby to double the number of tests that may be completed in generally the same time period.

Therefore, as shown in FIG. 2, a pair of loading stations 16 are provided along the front edge 18 of the horizontal supporting surface 12, with each loading station 16 being adapted to have positioned thereon a test-tube rack 20 having, in this embodiment, two rows or sets of twelve test tubes 22 each, with certain of the tubes 22 being intended to accommodate the formation and dissolving of fibrin-clots using varying concentrations of the manufactured enzyme to be tested and with the remaining test tubes 22 being intended to accommodate the formation and dissolving of fibrin-clots using standardized enzymes for analytical comparison purposes.

Intermediate the loading stations 16 and rearwardly thereof on the supporting surface 12 is a pipetting station 24 incorporating a pair of computer-controlled pipetting apparatus 26. Suitable computer-controlled pipetting apparatus 26 for use in pipetting station 24 would be the Hamilton Microlab 2200 Pipetting System. The pipetting station 24 includes reservoirs 28 of buffer, plasma, thrombin, fibrinogen, media and plasminogen solutions as well as production samples of the fibrin-clot dissolving product, specifically the enzyme urokinase, to be tested and standardized samples of the same enzyme against which corresponding concentrations of the production samples are to be analytically compared by a computer (not shown). Structural details of the pipetting apparatus 6 are not disclosed as the apparatus 26 is commercially available and the specific structure and operation of same is not a part of applicants' invention. Suffice it to say that each pipetting apparatus 26 is characterized by one or more vertically and horizontally movable arms each of which carries a pipette which, in accordance with a computer-controlled test program, selects the proper solutions, and amounts of same, from the reservoirs 28 of buffer, plasma, thrombin, fibrinogen, media and plasminogen and the proper dilutions of both production samples of the fibrin-clot dissolving enzyme and the standardized enzymes for the dispensing and mixing of same in said two sets of test tubes 22 whereupon fibrin-clots are formed in each test tube 22 with varying concentrations of production samples of the fibrin-clot dissolving enzyme associated therewith. Preferably, the pipetting apparatus 26 provides vortex dispensing and mixing of the various solutions and samples into the test tubes 22 so that the test tubes 22 need not be vibrated or capped and inverted to insure proper mixing of the contents thereof and the formation of fibrin-clots therein.

As best illustrated in FIGS. 1 and 2, the pipetting station 24 is provided with a cooling bath 30 for the solution and sample reservoirs 28 and for the racks 20 of test tubes 22 whereby same are all maintained at a temperature of 2°-8° C. to insure that the fibrin-clot dissolving enzymes are not activated at this point in the testing procedure. As shown in FIG. 2, a pair of rack guides 27 are provided in the cooling bath 30. As shown in FIGS. 1 and 2, a bottle of plasma reagent solution 28a is disposed in a cooling bath 30a. A refrigerant or coolant compressor 29, including a pump 31, is supported on the frame structure 10, as shown in the lower left corner of FIG. 1.

The testing system further includes a pair of heated bead-drop stations 32 at opposite ends of the frame structure 10 (FIGS. 1 and 2) wherein very similar opaque beads 34 of glass or plastic are simultaneously and gently introduced into each test tube 22 and wherein a known-type fiberoptic timer (not shown) is provided for each test tube 22 for timing and reporting to a computer the length of time it takes each bead 34 to pass through the dissolved fibrin-clot therein, the fibrin-clot dissolving enzymes having become activated as a result of removal of the test tube rack 20 from the cooling bath 30 and transfer of same into a heated water bath 36 at the bead-drop station 32. As best illustrated in FIGS. 4, 5, 6 and 7, each bead-drop station 32 is characterized by the water bath 36 having a bench-like support 38 disposed therein upon which the test tube rack 20 may be supported for warming after leaving the pipetting station 24 and after a bead 34 has been introduced into each test tube 22. An agitator or stirrer 40 extends downwardly into the water bath 36 at one end thereof and has a heater 42 associated therewith for maintaining the water bath 36 at a temperature of 37° C. (+/−1°). As previously noted, the support 38 has a series of known-type fiberoptic timers associated therewith, one for each of the test tubes 22, for timing the passage of each bead 34 through its dissolved fibrin-clot, this timing information being communicated to the programmed computer controlling this testing system via cables, two bundles of which are shown at 44 in FIGS. 4–7. Photo eye converters 33 for the fiberoptic timers are provided at each bead-drop station 32, as shown in FIGS. 1 and 3.

As shown in FIGS. 4–7, each test tube rack 20 is provided with a lower rectangular plate 46 having two parallel, longitudinally disposed rows of generally semi-cylindrical depressions 48 for receiving the lower ends of the plurality of test tubes 22, an upper rectangular plate 50 having two rows of openings 52 which are of a size to receive the test tubes 22 therethrough and which are vertically aligned with the depressions 48, and four corner posts 54 which support the upper plate 50 above the lower plate 46 a distance which is approximately two-thirds the height of the vertically disposed test tubes 22 carried in the rack 20. As illustrated at 56 in FIGS. 4, 5, and 7, the water level in the water bath 36 is preferably maintained at a level which is approximately one quarter of an inch above the upper level of the contents of the test tubes 22, but clearly below the open upper ends thereof, when a rack 20 of tubes 22 is supported on the bench-like support 38. This level insures most effective warming of the contents of the test tubes 22 and most accurate test results.

Each test tube rack 20 is also provided at the mid-section of its forward edge 58 with an upstanding grippable member 60 which, as will be further discussed herein, is used in transporting the rack 20 from station to station of the subject testing system.

Figure 4:
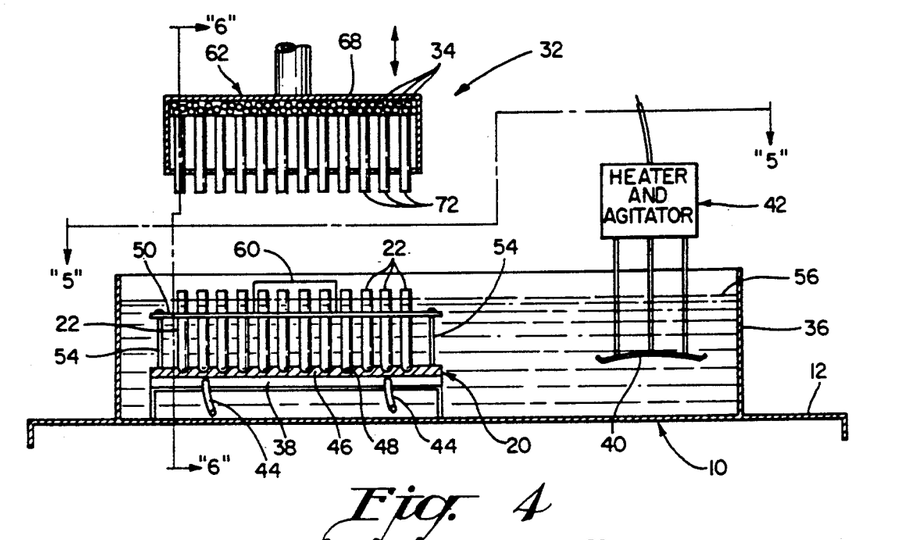
FIG. 4 is an enlarged partial vertical section view through one of the bead-drop stations and taken generally along line 4—4 of FIG. 2.
Figure 5:
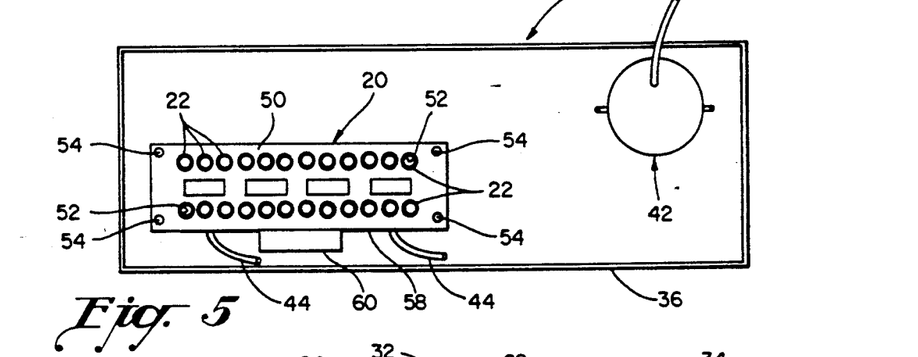
FIG. 5 is a top plan view of the bead-drop station of FIG. 4 taken generally along line 5—5 of FIG. 4.
Figure 6:
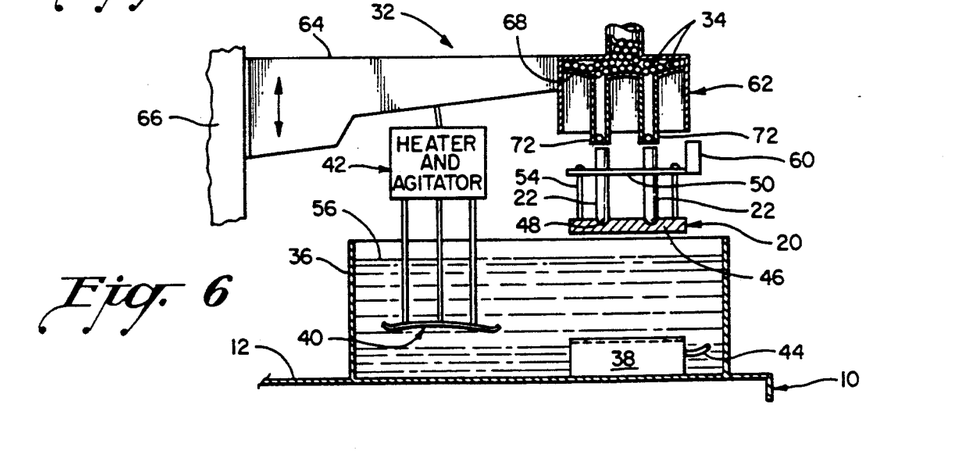
FIG. 6 is a vertical sectional end view of the bead-drop station of FIGS. 4 and 5 taken generally along line 6—6 of FIG. 4 with the bead-drop head and the rack of test tubes shown in their bead-dropping positions.
Figure 7:
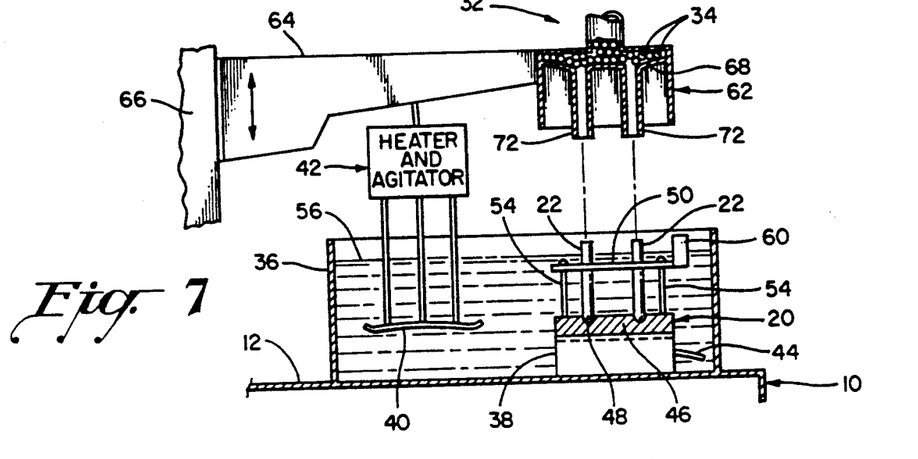
FIG. 7 is a vertical sectional end view similar to FIG. 6 but with the rack of test tubes in its lowered warming position.

As best illustrated in FIGS. 4, 6, and 7, each bead-drop station 32 includes a generally rectangular bead-supply head 62 which is mounted on one end of an arm 64 which is supported at its other end on a frame member 66 for vertical movement relative thereto. The bead-supply head 62 is disposed directly above the bench-like support 38 disposed in the water bath 36 and is movable vertically, the power source for the vertically movable head 62 being under the control of a programmable computer of this testing system.

Each bead-supply head 62 is provided in its upper portion with a manifold-like reservoir 68 which is fillable with the opaque beads 34 which are substantially identical in shape and weight. Extending downwardly from the underside of the manifold-like reservoir 68 are two rows, twelve in each row, of vertically disposed bead-delivery tubes 72, each of which is vertically aligned with one of the open-topped test tubes 22 in a rack 20. The upper ends of the delivery tubes 72 are openable to the manifold-like reservoir 68 and any one of several well-known mechanisms old in the art is provided for simultaneously releasing a single bead 34 into each of the 24 delivery tubes 72 at a programmed command from the computer. As the specific structure of the old-in-the-art release mechanism comprises no part of applicants' invention, no specific release mechanism is shown in the drawings. The release mechanism is programmed, of course, to be operable only when the bead-supply head 62 is in its position, as shown in FIG. 6 with the bottom ends of the delivery tubes 72 immediately adjacent the open upper ends of the test tubes 22 so that the delivery of the beads 34 into the tubes 22 in which the fibrin-clots have been formed is as gentle as possible.

As previously noted, the water bath 36, into which the rack 20 of test tubes 22 is then lowered to be positioned on the bench-like support 38, warms up the test tubes 22 and the clotted contents thereof whereby the clot-dissolving enzyme being tested and the plasminogen enzyme become active in the test tubes 22 to dissolve the fibrin-clots and permit passage of the beads 34 therethrough to the bottom of the test tubes 22. The previously-mentioned fiberoptic timers associated with each of the clotted test tubes 22 are automatically triggered simultaneously by the programmed computer upon the aforesaid simultaneous release of a single bead 34 into each of the twenty four clotted test tubes 22 with the breaking of the timers' light beams by the beads 34, which are preferably black or otherwise opaque, stopping the timers and providing measured time periods in which each clot was dissolved sufficiently to permit passage of its associated bead 34 therethrough, which time periods are received and recorded by the programmed computer for analysis thereby to provide test results as to the enzyme production samples being tested.

The rack 20 of unclotted test tubes 22 is then moved back to its initial loading station 16 where the used tubes 22 may be removed and disposed of after which the rack 20 may be loaded with a fresh set of test tubes 22 for the next test cycle.

To provide automatic movement of the test tube racks 20 from the loading stations 16 to the pipetting station 24, then to the bead-drop stations 32, and finally back to the loading stations 16 for unloading, a pair of commercially available robotic pick-and-place apparatus 74 are provided which operate automatically in accordance with the computer-controlled test program. Each robotic apparatus 74 is characterized by pick-up and release means, in the form of gripping fingers 76, on the end of an arm 78 which is movable both horizontally and vertically under the control of the programmed computer. The gripping fingers 76 are engageable with the sides of the grippable member 60 provided on each of the test tube racks 20. One commercially available robotic apparatus that would be suitable for use in this testing system would be a P.H.D. brand pick-and-place unit. As shown in the drawings, the pick-and-place robotic apparatus 74 is provided with known-type rotation apparatus 77 (FIGS. 1 and 3) and solenoid valves 79 (FIG. 1).

Figure 8:
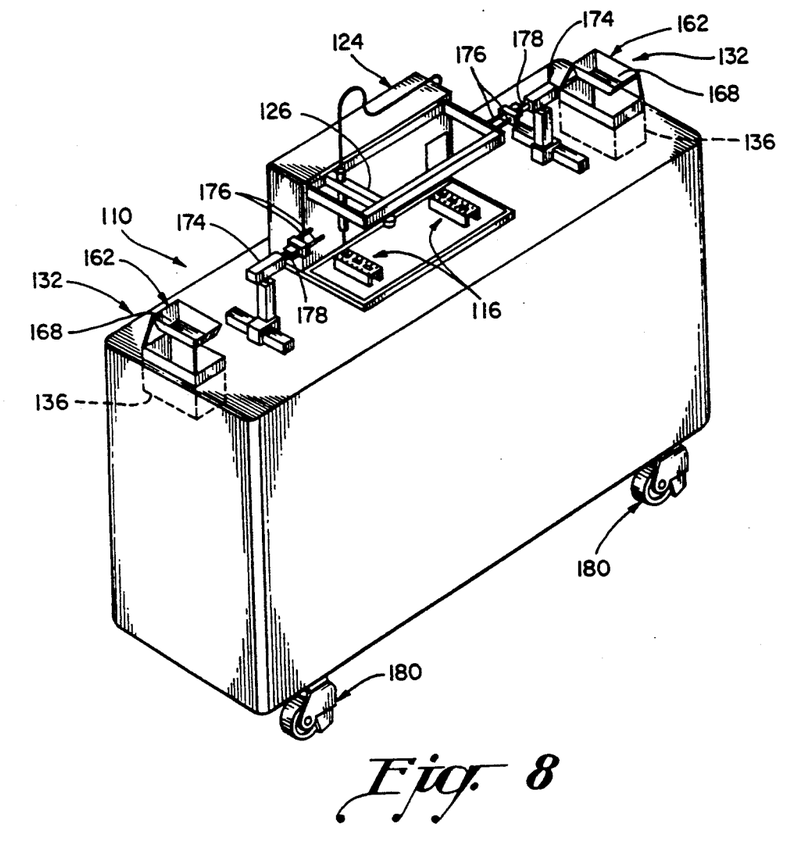
FIG. 8 is a diagrammatic perspective view of another embodiment of the invention.

A somewhat simpler form of the invention is shown in FIG. 8 wherein a table-like frame structure 110 is provided with a single pipetting apparatus 126 having a pair of test-tube rack loading stations 116 associated therewith, a pair of robotic apparatus 174 each of which has a pair of rack-gripping fingers 176 on an arm 178, and a pair of bead-drop stations 132 shown diagrammatically.

Both the frame structures 10 and 110 are provided with vertically movable wheels 80 and 180, respectively, which may be raised into out-of-the-way storage positions and lowered to facilitate movement of the frame structures from one location to another.

To conduct a quality-control test of production samples of a clot-dissolving enzyme, specifically urokinase, it is only necessary for a technician to fill the solution and sample reservoirs 28, check the levels and temperatures of the cooling baths 30 and 30a and the heated water baths 36, make sure the manifold-like bead reservoirs 68 are loaded with a sufficient number of beads 34, fill the test tube racks 20 with clean test tubes 22 and place them at the loading stations 16, and then activate the computer which has been pre-programmed for the desired testing sequence. Commercially available controls for this testing system may include a Square D PLC and an IBM PC. A "start and stop" station 82, including an "emergency stop" button, is shown in FIGS. 1 and 3.

As previously noted herein, under the control of the programmed computer the loaded test tube racks 22 are picked up by one of the robotic apparatus 74, transported to the pipetting station 24 where the pipetting apparatus 26 provides vortex dispensing and mixing of the proper mix of solutions, standards, and production samples for each test tube 22 for the development of fibrin-clots of varying concentrations, the solution reservoirs 28, production samples, and the test tubes 22 and their contents being kept at a cooled temperature so as not to activate the clot-dissolving enzymes at this stage of the testing procedure.

After the proper length of time for formation of the fibrin (blood) clots in the test tubes 22, approximately one minute, the rack 20 of clot-containing tubes 22 is transported by the robotic apparatus 74 to the bead-drop station 32 with the rack 20 being accurately positioned with the vertically disposed test tubes 22 vertically aligned beneath the delivery tubes 72 carried on the bead-supply head 62, which head 62 is then moved downwardly into the position shown in FIG. 6 under control of the computer. At the proper moment in the testing program, the bead-drop release apparatus is activated by the computer whereby, simultaneously, a single bead 34 is delivered gently into the open upper end of each of the test tubes 22 and the fiberoptic timers associated with each test tube 22 are activated. Then, still under the programmed control of the computer, the rack 20 of clot-and-bead-containing test tubes 22 is lowered into the heated water bath 36 onto the bench-like support 38 (FIG. 7). Each fiberoptic timer will then be shut down by the bead 34 falling through its clot, when same has been sufficiently dissolved, and blocking the light from the fiberoptic timer with the length of time for each clot to have been sufficiently dissolved to permit passage of its bead 34 therethrough on its way to the bottom of its tube 22 being transmitted to the computer where it is recorded. These recorded time periods permit automatic analysis and determination by the computer as to whether or not the production samples meet their required specifications.

The test tube rack 20 carrying the dissolved clots is then transported back to the loading station 16 by the robotic apparatus 74 where the tubes are unloaded by a technician so that a fresh rack 20 of test tubes 22 may be positioned in the loading station 16 preparatory for a further test run or cycle.

With the testing system shown in FIGS. 1-7, two test cycles or one complete sample may be run either simultaneously or at spaced intervals. However, with the somewhat simplified testing system shown in FIG. 8, the simultaneous test runs would not be possible. This testing system is characterized by the pair of loading stations 116 associated with a pipetting station 124 having the single pipetting apparatus 126, the pair of bead-drop stations 132, and the pair of robotic apparatus 174 each of which has the pair of gripping fingers 176 provided on the end of the vertically and horizontally movable arm 178. With this system, the dispensing and mixing of solutions, production samples, etc. in the second rack 120 of test tubes 122 would not be initiated by the computer until the first rack 120 of test tubes 122 had been transported from the pipetting station 124 to its bead-drop station 132. Otherwise the operation of the two system would be very similar.

Several different programs could be developed for the testing system disclosed herein. Being substantially fully automated, this system provides consistent results as accuracy and efficiency of operation performance are not operator dependent. As some testing could incorporate bio-hazardous material, minimal human presence and contact results from the automation aspect of this testing system.

Typically, each assay run of forty eight test tubes 22 will include both varying concentrations of the production samples in most of the test tubes 22 and standard curve dilutions in the remaining test tubes 22. In most tests, duplicate dilutions or concentrations of both samples and standards are provided in each pair of test tubes (adjacent tubes in the two rows) with the bead-time reading for the concentration therein being the average of that pair, unless the bead-time difference between the two is too great which would indicate a problem. In certain tests, the standard dilutions would be dispensed into the first three pairs of test tubes with the production samples being dispensed into the next nine successive pairs of tubes starting with the lowest concentrations. In other tests, the standards and production samples may be dispensed alternately into adjacent pairs of test tubes. The filling time for the twenty four test tubes 22 in a single rack 20 should average approximately five minutes.

Software for the computer, which should be provided with a monitor (also not shown), a printer 84 (on a printer table 86), and a disc drive 88, is programmed to provide all machine control functions including robotic pick-and-place control and bead-drop control, all pipetting functions, and collection of raw timer data and filing of same. Also shown in FIG. 3 of the drawings are a pump 90 for dispensing reagent and a pipetter tip wash station 92. Further, if desired, the system may be provided with a Plexiglas cover 94 including a door 94a providing access thereto. An "on demand" bar code printer (not shown) could be added to label assays and samples, which labels could be read by a scanner and entered into the computer.

While there has been shown and described two possible embodiments of the invention, it will be obvious to those skilled in the art that changes and modifications may be made without departing from the invention, and it is intended by the appended claims to cover all such changes and modifications as fall within the true spirit and scope of this invention.

We claim:

1. An automated testing system for quality testing production samples of a blood-clot dissolving product comprising,
   a) a frame structure having a horizontally disposed support surface,
   b) a loading station on said support surface for receiving a test tube rack containing a plurality of test tubes,
   c) a pipetting station on said support surface characterized by an automatic computer-controlled pipetting apparatus and by reservoirs of buffer, media, plasma, fibrinogen, thrombin, and plasminogen solutions as well as production samples of the blood-clot dissolving product to be tested, all of which solutions are maintained at a certain cooling temperature of from 2°-8° C., which pipetting apparatus comprises means for providing vortex dispensing and mixing of said solutions and production samples in test tubes positioned in said test tube rack in accordance with a computer-controlled test program for controlling formation of fibrin clots in each of said test tubes,
   d) a heated bead-drop station on said support surface wherein substantially identical beads are simultaneously introduced into each test tube and wherein means are provided for timing, reporting and recording the time required for each bead to reach the bottom of said test tubes upon dissolving of said fibrin-clot therein,
   e) a robotic pick-and-place apparatus on said frame structure having pick-up and release means at the end of an arm thereof which arm comprising means for moving both vertically and horizontally, wherein said robotic apparatus comprising means for picking-up, said test tubes said test tube rack filled with empty test tubes from said loading station and for moving said test tube rack to said pipetting station and then to said heated bead-drop station and then back to said loading station in accordance with said computer
   controlled program, and
   f) a programmable computer for controlling said robotic apparatus, said pipetting apparatus, and the operations at said bead-drop station and for receiving and recording the results of said product testing.

2. The automated testing system of claim 1 wherein a pair of loading stations, a pair of robotic apparatus, and a pair of bead-drop stations are provided on said support surface and wherein a computer program is provided which results in twice as many sample tests being conducted.

3. The automated testing system of claim 2 wherein said pair of loading stations are both disposed at said pipetting station whereby said pair of robotic apparatus are programmed to move a pair of racks of test tubes only from said pipetting station to said pair of bead-drop stations and back to said pair of loading stations.

4. The automated testing system of claim 1 wherein said frame structure is mounted on rollers to facilitate movement of same from place to place.

5. The automated testing system of claim 1 wherein means are provided at said pipetting station for maintaining said reservoirs of solutions and said test tubes, after said samples and solutions have been dispensed and mixed therein, at a cooling temperature of from 2°-8° C. until said test tube rack is moved from said pipetting station to said bead-drop station.

6. The automated testing system of claim 1 wherein a water bath heated to a temperature of 37° C. (+/−1°) is provided at said bead-drop station for receiving said rack of test tubes.

7. The automated testing system of claim 1 wherein fiberoptic timer means are provided at said bead-drop station for each test tube, each fiberoptic timer means comprises being activated for measuring the length of time required for the fibrin-clot in that test tube to dissolve.

8. The automated testing system of claim 1 wherein the fibrin-clot dissolving product to be tested is the enzyme urokinase.

9. An automated testing system for quality testing production samples of urokinase, a clot dissolving enzyme, comprising,
   a) a test tube rack loading station,
   b) a test tube rack containing a plurality of test tubes,
   c) a fibrin-clot forming station characterized by reservoirs of fibrin-clotting solutions and production samples of urokinase to be tested, comprising means for maintaining temperature of said solutions and samples at said station at 2°-8° C., and by an automatic computer-controlled pippeting apparatus comprising means for providing dispensing and mixing of said solutions and production samples in said test tubes positioned in said rack, when said rack is disposed at said fibrin-clot forming station, in accordance with a computer-controlled test program, for controlling formation of fibrin-clots in each of said test tubes,
   d) a bead-drop station comprising means for introducing substantially similar opaque beads into each test tube, by a heated water bath for said rack of fibrin-clot-containing test tubes into which said beads were introduced to aid dissolution of said fibrin-clots as a result of warming thereof, and further comprising means for timing, reporting and recording the time required for each bead to pass through said fibrin-clot upon dissolution thereof,
   e) a robotic apparatus having pick-up and release means for picking up said test tube rack filled with empty test tubes from said loading station and for moving test tube rack to said fibrin-clot forming station and then to said bead-drop station and then back to said loading station for unloading of said rack in accordance with said computer-controlled program, and
   f) a pre-programmed computer for controlling said robotic apparatus, said pipetting apparatus, and the operations at said bead-drop station and for receiving and recording the results of said testing of said production samples of urokinase.

10. The automated testing system of claim 9 wherein vortex dispensing and mixing of said solutions and production samples in said test tubes is provided at said fibrin-clot forming station.

11. The automated testing system of claim 9 wherein fiberoptic timer means are provided at said bead-drop station for each test tube, each fiberoptic timer means comprises being activated for measuring the length of time required for the fibrin-clot in that test tube to dissolve.

12. The automated testing system of claim 9 wherein said test tube rack loading station, said fibrin-clot forming station, said bead-drop station, and said robotic apparatus are all mounted on a frame structure mounted on rollers.

* * * * *